United States Patent [19]

Webster et al.

[11] Patent Number: 4,999,329
[45] Date of Patent: Mar. 12, 1991

[54] CATALYST FOR THE PRODUCTION OF POLYALKYLENEPOLYAMINES

[75] Inventors: Stephen J. Webster, Angleton; Lester L. Melton, Richwood, both of Tex.

[73] Assignee: The Dow Chemical Company, Midland, Mich.

[21] Appl. No.: 418,291

[22] Filed: Oct. 6, 1989

[51] Int. Cl.$^5$ .................. B01J 27/02; B01J 27/06; B01J 27/14; B01J 27/16

[52] U.S. Cl. .................. 502/202; 502/208; 564/479

[58] Field of Search .............. 502/202, 208; 564/479

[56] References Cited

U.S. PATENT DOCUMENTS 3,291,848 12/1966 Nixon ........................ 502/208 X
4,806,517 2/1989 Vanderbool et al. .......... 502/208

FOREIGN PATENT DOCUMENTS 0166157 1/1986 European Pat. Off. ............ 502/208

Primary Examiner—W. J. Shine

[57] ABSTRACT

A catalyst for making polyalkylenepolyamines by the reaction of a monoalkanolamine with an alkyleneamine which contains phosphorus and fluorine on a metal oxide support, the metal being selected from Groups IIIA, IIIB, IVB and VB of the periodic chart. The surface of a support, e.g. titania, is impregnated with at least one compound which contains fluorine and one which contains phosphorus. The same compound can contain both elements, e.g. a fluorophosphoric acid, or two or more compounds, which together contain the required elements, can be employed.

14 Claims, No Drawings

CATALYST FOR THE PRODUCTION OF POLYALKYLENEPOLYAMINES

BACKGROUND OF THE INVENTION

Polyethylenepolyamines are commonly made industrially by the reaction of ethylene dichloride (EDC, 1,2-dichloroethane), with ammonia at elevated temperature and pressure to form a mixture of amine hydrochlorides. The amine hydrochlorides are treated with aqueous caustic to neutralize the hydrochloride and NaCl is produced as a by-product. Excess ammonia is removed and the amines are separated by distillation under vacuum in order to avoid degradation. The composition of the amine mixture can be varied by recycling one of the product amines which results in an increase in the amount of the amine next higher in the series to the one recycled. The process described is energy intensive because of the separations involved.

Another process (U.S. Pat. No. 4,647,701) for producing ethyleneamines involves reductive amination of monoethanolamine, which is passed over a nickel catalyst in the presence of hydrogen at a temperature of 150° C. to 225° C. and a pressure of 35 to 400 atm. In addition to the ethylenediamine (EDA) and diethylenetriamine (DETA), piperazine and substituted piperazines are produced. Although this process overcomes some of the difficulties of the EDC-NH$_3$ process, it is unable to produce the desired higher polyamines without the concurrent production of undesired substituted piperazines.

More recently acid dehydration catalysts have been employed to react an alkanolamine with ammonia or an amine to produce non-cyclic polyamines. In U.S. Pat. No. 4,036,881 a catalyst for making polyamines is disclosed which contains a phosphorous substance, e.g. boron phosphate. Other patents for the reaction include phosphorus supported on titania (U.S. Pat. No. 4,524,143), zirconia (U.S. Pat. No. 3,358,029) and zirconium silicate (U.S. Pat. No. 3,321,506). Group IIIB metal acid phosphates (U.S. Pat. No. 4,463,193) have also been employed for the purpose.

Various sulfates, nitrates and phosphates also have been disclosed as catalysts for making amines. In a related reaction, a fluorosulfonic acid catalyst has been disclosed as useful for reacting an alkylene oxide with ammonia or an amine to prepare an alkanolamine (U.S. Pat. No. 4,605,769).

SUMMARY OF THE INVENTION

A catalyst for making a polyalkylenepolyamine by reacting a monoalkanolamine with an alkyleneamine which comprises (1) a metal oxide support, e.g., Al$_2$O$_3$ or TiO$_2$, which is impregnated with (2) a compound containing fluorine and phosphorus, e.g. fluorophosphoric acid or (3) a mixture of at least two compounds, one of which contains phosphorus and another fluorine, e.g. H$_3$PO$_4$ and HF.

A second aspect of the invention is the process for making said catalyst which comprises contacting the support material with a solution of compounds in (2) or (3) above for a time sufficient to impregnate at least the surface of the support. Alternatively, the support can be contacted with a solution of one of the compounds, followed by contacting with a solution of the second, one of which contains phosphorus and the other fluorine. Each of the solutions must remain in contact with the support material for a time sufficient to impregnate at least the surface of the support.

DETAILED DESCRIPTION OF THE INVENTION

Metal oxides, such as alumina, titania and the oxides of the other metals of Groups IIIA, IIIB, IVB and VB of the periodic chart are used as catalyst support materials. Representative of these groups are the oxides of boron (IIIA), lanthanum (IIIB), titanium and zirconium (both IVB) and tantalum (VB).

The metal oxide employed as the catalyst support can be used in any acceptable form, e.g. spheres, rings, cylinders and the like. The support material is impregnated by contacting it with a solution of a compound containing fluorine and phosphorus. This is generally accomplished by soaking the support in the solution for a sufficient time to obtain at least a surface impregnation of the support material. Alternatively, one can use a mixture of compounds, at least one of which contains fluorine and another phosphorous, so long as the resulting catalyst contains both phosphorous and fluorine.

Thus, for example, phosphorous-containing compounds useful in the catalysts of the invention are boron phosphate, phosphoric acid, phosphorous acid, chlorophosphoric acid, phosphoryl chloride, phosphorus pentoxide and thiophosphoryl chloride; those which contain fluorine that are useful include, for example, hydrofluoric acid, fluorosulfonic acid and difluorophosphoric acid.

The following examples illustrate the process of obtaining the catalysts of the invention:

Catalyst Preparation

Procedure I. Non-fluorine-containing Catalysts (Comparative)

The titania catalyst support was crushed and sieved to give a particle size within the range 170–850 pm. The support was then placed in a glass five-neck one liter round-bottom flask, fitted with nitrogen purge, reflux condenser, mechanical stirrer, thermometer and temperature controller. Approximately 500 mL of the liquid catalyst (aqueous solution or undiluted) was placed in the flask and the mixture brought to a low boil with total reflux and held there for two hours. The solution was then allowed to cool to 60° C. before filtering off the solution from the treated support. The treated support was washed with copious amounts of deionized water and then dried in a vacuum oven at 90° C. for 16 hours under full (20" Hg) vacuum. After cooling to room temperature, the catalyst was loaded into the reactor tube.

Procedure II. Catalysts of the Invention

To make a fluorine-containing catalyst of the invention 100 cc of the same type of titania as in Procedure I was treated with 100 g difluorophosphoric acid (HPO$_2$F$_2$.0.5 H$_2$O). A stainless steel beaker was substituted for the glass flask and instead of boiling the solution, it was cooled to 10° C. and maintained at that temperature for two hours after the support was added. The low temperature reduced the tendency of the acid to attack and deteriorate the support material and, of course, the tendency of attack on the container was reduced because of the substitution of stainless steel for glass. In like manner another catalyst was made by treating titania with monofluorophosphoric acid (H$_2$PO$_3$F). Mixtures of fluorine-containing and phosphorous-containing compounds were also employed to make catalysts of the invention.

In other preparations titania was treated as in Procedure I with phosphoric acid ($H_3PO_4$) and boron phosphate ($BPO_4$) and as in Procedure II with hydrofluoric acid (HF) so as to compare the catalysts of the invention with catalysts known to the art.

The reactant diamine and alkanolamine are contacted over the catalyst in any convenient manner. Preferably they are mixed and passed through a fixed bed of the catalyst in a tubular reactor. The pressure is conveniently from about 50 to about 5000 psig., preferably from about 750 to about 2500 psig. The temperature is maintained within the range of from about 180° to about 350° C., preferably from about 240° to about 290° C. The molar feed ratio of the amine to alkanolamine is from about 0.5 to about 10, preferably from about 1.0 to about 4.0.

The following examples demonstrate the use of the above-prepared catalysts. The comparative examples are indicated by the letters A, B, C, etc. while the examples of the invention are indicated by numerals.

EXAMPLE 1

The titania-supported $H_2PO_3F$ catalyst (20.8 cc) was placed in a stainless steel reactor tube (0.43" I.D.×12" long) to a depth of ca. 10" and insulated with ca. 3" of rock wool and foamed glass. The surface area of the titania support prior to impregnation with the catalyst was 205 m²/g. Glass wool and an inert ceramic material were placed in each end of the reactor. The feed line for the reactants was coiled around the reactor to permit preheating of the reactants. A positive displacement pump was used to control the flow of reactants to the reactor. Solid state temperature controllers were employed. An adjustable relief valve was used as a pressure controller.

Ethylenediamine (EDA) and monoethanolamine (MEA) were reacted at a 2/1 mole ratio, respectively, over the above catalyst. The analysis of the effluent was accomplished using a Hewlett Packard Model 5890 capillary column gas chromatograph with a DB-5 fused silica column obtained from J&W Scientific Co.

EXAMPLE 2

The same amount of the titania-supported difluorophosphoric acid ($HPO_3F_2$) catalyst prepared above was placed in a reactor identical to that described in Example 1 and EDA and MEA, again at a 2/1 ratio, were passed over this catalyst.

The catalysts of Examples 1 and 2 were run at various temperatures, but at the same flow rate, pressure and feed ratios. The conditions were:
Pressure=3000 psig (204 atm.),
Flow rate=1.0 mL/min.,
Molar feed ratio (EDA/MEA)=2/1

EXAMPLE 3

In an alternative procedure a mixture of phosphoric ($H_3PO_4$) and hydrofluoric (HF) acids were employed at a mol ratio of 1/1 to treat a titania support. This was accomplished in the manner of Procedure II. The same amount (20.8 cc) of this catalyst was then placed in a reactor identical to that described in Example 1 and EDA and MEA, again at a 2/1 ratio, were passed over this catalyst.

Results of the product analyses for the catalysts of Examples 1, 2 and 3 are shown in Tables I, II and III, respectively. The components of the product mixture are identified in the following Tables as aminoethanolamine (AEEA), diethylenetriamine (DETA), triethylenetetramine (TETA), tetraethylenpentamine (TEPA), pentaethylenehexamine (PEHA), piperazine (PIP) and aminoethylpiperazine (AEP).

TABLE I

| | | ($H_2PO_3F$) | | | | | |
|---|---|---|---|---|---|---|---|
| Run No. | Temp. (°C.) | AEEA | DETA | TETA | TEPA | PEHA | PIP AEP |
| 1 | 210 | 1.2 | 6.7 | 0.5 | — | — | — — |
| 2 | 230 | 3.6 | 17.6 | 3.9 | 0.47 | — | 0.38 0.2 |
| 3 | 250 | 0.6 | 28.5 | 14.1 | 3.98 | 1.03 | 1.19 1.2 |
| 4 | 270 | 0.1 | 25.7 | 17.7 | 6.87 | 2.16 | 3.05 3.4 |
| 5 | 290 | 0.6 | 20.9 | 19.9 | 7.85 | 2.79 | 6.43 7.4 |

TABLE II

| | | ($HPO_3F_2$) | | | | | |
|---|---|---|---|---|---|---|---|
| Run No. | Temp. (°C.) | AEEA | DETA | TETA | TEPA | PEHA | PIP AEP |
| 1 | 210 | 0.9 | 3.9 | — | — | — | 0.1 — |
| 2 | 230 | 4.4 | 18.7 | 5.1 | 0.78 | — | 0.44 0.3 |
| 3 | 250 | 0.5 | 29.1 | 15.4 | 4.71 | 1.17 | 1.46 1.4 |
| 4 | 270 | 0.2 | 24.7 | 17.4 | 6.76 | 2.13 | 3.38 3.5 |
| 5 | 290 | 0.5 | 18.7 | 19.6 | 7.92 | 3.21 | 8.74 9.5 |

TABLE III

| | | ($H_3PO_4$ + HF) | | | | | |
|---|---|---|---|---|---|---|---|
| Run No. | Temp. (C.) | AEEA | DETA | TETA | TEPA | PEHA | PIP AEP |
| 1 | 210 | 1.0 | 3.7 | — | — | — | — — |
| 2 | 230 | 4.0 | 14.1 | 2.5 | — | — | 0.29 0.1 |
| 3 | 250 | 0.6 | 27.1 | 12.0 | 3.12 | 0.58 | 1.03 1.0 |
| 4 | 270 | 0.1 | 26.8 | 16.0 | 5.69 | 1.55 | 1.79 2.1 |
| 5 | 290 | 0.5 | 22.3 | 18.9 | 6.99 | 2.41 | 5.31 6.2 |

EXAMPLE A (COMPARATIVE)

The catalyst prepared according to Procedure I was employed in the same EDA+MEA reaction as in Examples 1-3 above (using an identical reactor and the same temperatures, pressure, flow rate and feed ratio). The catalytic material used to treat the support was $H_3PO_4$. The results are shown in Table IV.

TABLE IV

| | | ($H_3PO_4$) | | | | | |
|---|---|---|---|---|---|---|---|
| Run No. | Temp. (°C.) | AEEA | DETA | TETA | TEPA | PEHA | PIP AEP |
| 1 | 210 | — | — | — | — | — | — — |
| 2 | 230 | — | — | — | — | — | — — |
| 3 | 250 | — | 0.4 | — | — | — | — — |
| 4 | 270 | — | 6.4 | 0.8 | — | — | 0.25 0.2 |
| 5 | 290 | 0.10 | 19.1 | 8.0 | 2.93 | 0.18 | 1.94 2.40 |

Conversions of MEA and EDA for Tables I, II, III and IV are shown in Table V.

TABLE V

| | | Percent Conversions Run # | | | | |
|---|---|---|---|---|---|---|
| Table No. | Amine | 1 | 2 | 3 | 4 | 5 |
| I | MEA | 12.11 | 53.89 | 100 | 100 | 100 |
| I | EDA | 6.94 | 9.66 | 21.61 | 35.63 | 44.87 |
| II | MEA | 6.08 | 56.84 | 100 | 100 | |
| II | EDA | 4.13 | 14.21 | 27.57 | 41.10 | 50.16 |
| III | MEA | 6.05 | 41.56 | 98.28 | 100 | 100 |

TABLE V-continued

| Table No. | Amine | Percent Conversions Run # | | | | |
|---|---|---|---|---|---|---|
| | | 1 | 2 | 3 | 4 | 5 |
| III | EDA | 3.33 | 8.31 | 13.13 | 26.80 | 38.59 |
| IV | MEA | — | — | 1.9 | 19.11 | 66.87 |
| IV | EDA | — | — | — | — | 15.83 |

We claim:

1. A catalyst for making a polyalkylenepolyamine by reacting a monoalkanolamine with an alkylene-amine which comprises a metal oxide support the surface of which is impregnated with at least one compound which contains phosphorus and at least one which contains fluorine wherein the metal oxide support is an oxide of a metal selected from Groups IIIA, IIIB, IVB or VB of the periodic chart and (A) wherein the phosphorus and fluorine are in the same compound and wherein the compound is a fluorophosphoric acid or (B) wherein the phosphorus and fluorine are in different compounds and wherein the phosphorus compound is boron phosphate, phosphoric acid, phosphorus pentoxide, phosphorous acid, phosphoryl chloride, thiophosphoryl chloride or chlorophosphoric acid; and the fluorine containing compound is hydrofluoric acid, fluorosulfonic acid, or difluorophosphoric acid.

2. The catalyst of claim 1 wherein (A) the phosphorus and fluorine are in the same compound and wherein the compound is monofluorophosphoric or difluorophosphoric acid or (B) the phosphorus and fluorine are in different compounds and wherein the phosphorus compound is phosphoric acid and the fluorine containing compound is hydrofluoric acid; the phosphorus compound is boron phosphate and the fluorine containing compound is fluorosulfonic acid; the phosphorus compound is phosphoric acid and the fluorine containing compound is difluorophosphoric acid; the phosphorus compound is phosphorus pentoxide and the fluorine containing compound is hydrofluoric acid; the phosphorus compound is chlorophosphoric acid and the fluorine containing compound is fluorosulfonic acid.

3. The catalyst of claim 1 wherein the phosphorus and fluorine are in the same compound.

4. The catalyst of claim 1 wherein the compound is a fluorophosphoric acid.

5. The catalyst of claim 2 wherein the compound is monofluorophosphoric acid.

6. The catalyst of claim 2 wherein the compound is difluorophosphoric acid.

7. The catalyst of claim 2 wherein the phosphorus compound is phosphoric acid and the fluorine containing compound is hydrofluoric acid.

8. The catalyst of claim 2 wherein the phosphorus compound is boron phosphate and the fluorine containing compound is fluorosulfonic acid.

9. The catalyst of claim 2 wherein the phosphorus compound is phosphoric acid and the fluorine containing compound is difluorophosphoric acid.

10. The catalyst of claim 2 wherein the phosphorus compound is phosphorus pentoxide and the fluorine containing compound is hydrofluoric acid.

11. The catalyst of claim 2 wherein the phosphorus compound is chlorophosphoric acid and the fluorine containing compound is fluorosulfonic acid.

12. The catalyst of claim 5 wherein the metal oxide support is titanium oxide.

13. The catalyst of claim 6 wherein the metal oxide support is titanium oxide.

14. The catalyst of claim 7 wherein the metal oxide support is titanium oxide.

* * * * *